United States Patent [19]

Hennequin

[11] Patent Number: 4,714,330
[45] Date of Patent: Dec. 22, 1987

[54] DEVICE FOR DETECTING AND/OR MEASURING VISUAL DEFICIENCIES

[75] Inventor: Jean-Claude Hennequin, Lizy sur Ourco, France

[73] Assignee: Essilor Internationale, Creteil, France

[21] Appl. No.: 772,327

[22] Filed: Sep. 4, 1985

[30] Foreign Application Priority Data

Sep. 7, 1984 [FR] France .................. 84 13766

[51] Int. Cl.$^4$ .............................. A61B 3/02
[52] U.S. Cl. .................. 351/239; 351/237; 351/243
[58] Field of Search ............ 351/239, 240, 241, 242, 351/243, 244, 237

[56] References Cited

U.S. PATENT DOCUMENTS 3,011,394 12/1961 Sherman et al. ............ 351/239
4,550,990 11/1985 Trispel et al. ............... 351/244 X

FOREIGN PATENT DOCUMENTS 3013013 10/1981 Fed. Rep. of Germany ...... 351/239

OTHER PUBLICATIONS

American Optical Vision, American Optical Co., p. 14 "A-O Project-O-Chart"Jul. 1934.
Optometric Weekly, American Optical Co., p. 50, Aug. 1967.

Primary Examiner—Rodney B. Bovernick
Attorney, Agent, or Firm—Burgess, Ryan & Wayne

[57] ABSTRACT

The present invention relates to a device for detecting and/or measuring visual deficiencies in which an image observable by a patient presents several series of test signs, each corresponding with one of the various levels of visual acuity, wherein each sign corresponding to a level of visual acuity is associated to a reference sign corresponding to a lower level of visual acuity and wherein frame 1 contains signs corresponding to a visual acuity of 1/10, another frame 2 to 2/10 and following frames correspond to visual acuities ranging by steps of 2/10 respectively from the value 4/10 to the value 10/10.

6 Claims, 1 Drawing Figure

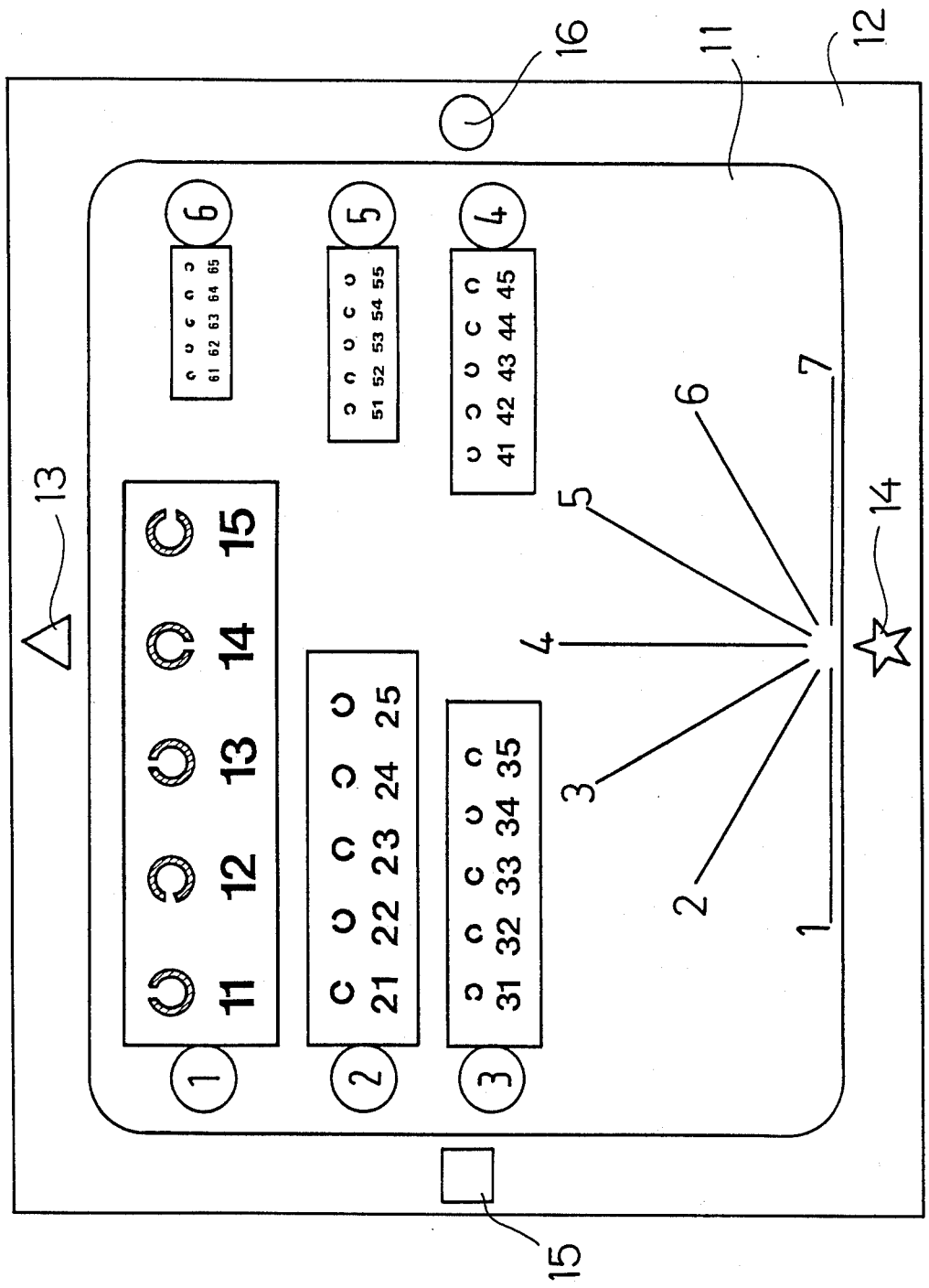

DEVICE FOR DETECTING AND/OR MEASURING VISUAL DEFICIENCIES

BACKGROUND OF THE INVENTION

Field of the Invention

The present invention concerns devices for detecting and/or measuring visual deficiencies, and more particularly to a device for measuring the level of visual acuity of a patient.

With a view to detecting visual deficiencies and determining the visual acuity of a patient, tests are usually carried out that consist of presenting the patient with real or virtual images of signs or patterns, the dimensions of which are well defined, especially in size and in thickness. These patterns represent, among others, letters or figures, geometrical signs or figures that have been especially devised for this use, such as the Landolt ring, i.e. rings or Landoldt C's, that are open according to a strictly defined geometry.

These images can be panels; they can be projected on a screen or be observed in an optical device under the form of virtual images. They can be produced, for example, from transparencies or slides or other supports that are generally transparent in order to favor the lighting thereof.

Numerous type of devices exist but up to now it has never been possible to overcome certain problems due to the element of doubt that remains for the experimenter with regard to the patient's reactions.

It is known that measuring the visual acuity is appreciated by values of which the maximum is 10, the value 10/10 corresponding to normal visual acuity and the decreasing values to an acuity that is progressively lower.

Various dispositions according to the prior art propose signs corresponding to acuities ranging by increments of tenths from 1/10 to 10/10, the smallest and finest signs corresponding to the highest acuity, the larger and thicker signs corresponding to lower levels of acuity.

This graduation of the sign series shown to the patient will require him to define up to which degree he is able correctly to identify the signs, starting, of course, by the largest ones. The definition of the limit degree is often delicate and the experimenter has, according to the techniques of the prior art, only few means of checking the accuracy of the definition.

SUMMARY OF THE INVENTION

The present invention allows, due to an appropriate device, to be sure of the accuracy of the indications given by the patient.

A certain number (normally 10) of groups of signs are shown to the patient, each group corresponding to a specific degree of visual acuity.

Each group is constituted by two sub-groups, one being comprised of test signs corresponding exactly to the degree of acuity displayed and the other one being comprised of reference signs corresponding to the lower degree of acuity, each one of these latter sub-groups being constituted by a reference system such as a system of numerals. Thus when a patient examines the group corresponding to his acuity limit, he will be able to better distinguish the reference signs forming the second sub-group and the test signs proper forming the first sub-group. This also presents the advantage that when the patient thinks that he is identifying a sign of the first sub-group, he must be able to indicate without fault the reference of said sign.

This advantage is that much greater when the patient is examining an image in an apparatus (as is the case, for example, according to U.S. Pat. No. 4,412,729), since the experimenter can exert no direct control on the observations indicated by the patient, above all when virtual images are being examined through an eye-piece or similar device.

In the following description, and for the sake of greater clarity, reference will be made to an eye testing chart, it being well understood that the invention alo applies to any other support, transparent or not, provided that the patient can examine it directly or observe an image (real or virtual) thereof through any convenient optical means, the sole primarily important convenient optical means, the sole primarily important condition to be met being the value of the ratio "dimensions of the signs/distance between the eyes and the signals", which is indispensable for defining the visual acuity.

DESCRIPTION OF THE DRAWING

The single drawing depicts a test card containing 6 frames each containing test signs for the measurement of visual acuity, as well as additional signs for detecting and measuring visual deficiencies.

DETAILED DESCRIPTION OF A PREFERRED EMBODIMENT

In order to render more apparent the technical features and advantages of the present invention, an embodiment will now be described, it being understood that said embodiment is not limited to the specific embodiment or to the applications that can be made thereof. Reference will be made to the appended single figure that represents a chart according to the invention.

As stated herein-above, the test card shown or its image are presented to the patient according to defined standards relating to distances and sizes corresponding in fact to angle of view standard values. It will be supposed in this example that the chart is presented in the form of a slide or transparency projected onto a screen placed in front of the patient.

This slide or transparency presents a clear (or light) central portion 11 having a general rectangular form surrounded by a dark, possibly even opaque, portion 12.

In the central portion are traced a certain number of frames (for example 6) marked by encircled FIGS. 1 to 6.

The test signs of frame 1 correspond to a visual acuity of 1/10, those of frame 2 to an acuity of 2/10, and those of frames 3, 4, 5 and 6 to respective visual acuity levels ranging from 4/10 to 10/10 according to a stepwise progression of 2/10 from any one of frames 3 to 6 to the subsequent frame. In the embodiment shown, these test signs are Landoldt rings, well known to those skilled in the art.

The patient examining the image will be requested by the experimenter to observe the rings of the successive frames 1, 2, 3, etc.

This method corresponds to known techniques but there always remains an element of doubt in the mind of the experimenter as to the exactitude of the comments made by the patient and as to the relation between these oral comments and the sign effectively observed. The patient and the experimenter may indeed relate a given comment on one sign to some other sign.

According to the invention, in each frame 1, 2, 3, etc., each Landoldt ring or similar test sign is identified by a reference sign or marking located at close proximity to the test sign considered, for example, by a numeral the first digit of which corresponds to the number of the frame and thus to the number of tenths of which indicates the level of visual acuity. Thus the test signs of frame 1 are numbered 11, 12, 13, etc; those of frame 2 are numbered 21, 22, 23, and so on. However, it should be noted that one of the essential features of the present invention lies in the fact that in any given frame corresponding to a visual acuity A, the dimensions of the test sign numbers of numerals corresponds to an acuity level lower by at least 1/10 than said acuity A, i.e. to an acuity level equal to or lower than A-1/10.

Thus, in the embodiment shown, the numerals located outside frames 2 to 6 represent a visual acuity corresponding to that of the rings disposed in frames 1 to 5, respectively. Of course, at frame 1, it is possible to limit markings to acuity numbers of 1/10 but it is also possible to depart from the standards by using higher numerals, i.e. numerals corresponding to theoretical acuities lower than 1/10.

In a modified embodiment, ten frames may be provided, numbered 1 to 10 and comprising Landoldt rings corresponding to a visual acuity ranging from 1/10 (in the first frame) to 10/10 (in the tenth frame).

The device according to the invention is advantageous in that when the patient reaches the frame where his observations become uncertain, he must nevertheless still be able to read correctly the reference sign or numeral test sign observed, since this reference numeral is easier to read since its dimensions correspond to a visual acuity lower by one tenth than the acuity to which correspond the dimensions of the test sign designated or identified by the reference numeral.

This eliminates two doubts for the experimenter: on the one hand, it is thus ascertained that the patient's acuity limit has been reached, since he correctly reads the reference numerals, but fails to read correctly the corresponding test signs; on the other hand, the experimenter is satisfied that the patient describes a determined test sign as identified by its reference numeral and that there is no misunderstanding as to the sign observed.

Furthermore, to prevent the patient from making an error as to the orientation of the gap of a Landoldt ring by confusing (top and bottom, and especially left and right, which is a frequently occurring error), the chart is provided with orientation signs located above, below, on the left and on the right and formed, in the present example, respectively, by a triangle 13, a star 14, a square 15 and a circle 16, represented within light colour in the dark or opaque portion of the chart. It is also possible to give each sign a colour different from that of the other signs.

Therefore, in order to describe the position or orientation of the gap of the Landoldt ring that he observes, the patient will not have to announce "right", "left", "top" or "bottom", but simply "circle", "square", "triangle" or "star". The chart may also comprise any other conventional patterns, signs or symbols for detecting and/or measuring visual deficiencies.

It can thus be considered that the patient will be able to observe an image (directly on a chart or any other support, or in the form of a real image projected onto a screen, or in the form of a virtual image viewed through an optical viewing system), the size/distance from the eye ratio being defined according to conventional standards.

The invention thus can be adapted to numerous devices, especially to existing devices which have not given entirely satisfactory results up to now.

The invention is not limited to the embodiments described and shown herein. Many variants and modifications may be envisaged by those skilled in the art, without departing from the spirit and scope of the invention as defined in the appended claims.

I claim:

1. A device for measuring the level of visual acuity of a patient, comprising a test image which is adapted to be presented to the patient and which includes a plurality of visual acuity test sign series in which the test signs of each one of said series are so dimensioned that they correspond to a visual acuity level which is different from that of the test signs of any other one of said series, said series being so disposed in succession that each one of said test sign series corresponds to a visual acuity level higher by a predetermined increment than the visual acuity level to which corresponds the preceding test sign series, wherein said test signs are identified by different respective reference signs, each one of said reference signs being located at close proximity to the test sign which it identifies, and wherein the reference signs identifying respectively the test signs of any selected one of said series are so dimensioned that they correspond to the lower visual acuity level of the series immediately preceding said selected series.

2. A device according to claim 1, wherein said visual acuity test signs are Landoldt rings.

3. A device according to claim 1, wherein said reference signs are numerals.

4. A device according to claim 3, wherein said numerals each comprise at least two digits, one of the digits of any test sign numeral being indicative of the level of visual acuity to which corresponds the test sign identified by the numeral considered.

5. A device according to claim 2, wherein orientation symbols are provided which allow the orientation of said Landoldt rings to be defined by the patient.

6. A device according to claim 1, wherein each series of test signs and the reference signs identifying the same are located within a frame which is provided with a symbol indicating the level of visual acuity to which correspond the test signs of said frame.

* * * * *